United States Patent
Jimoh et al.

[11] Patent Number: 6,117,816
[45] Date of Patent: Sep. 12, 2000

[54] STORAGE-STABLE COMPOSITION CONTAINING EXOGENOUS CHEMICAL SUBSTANCE AND SILOXANE SURFACTANT

[75] Inventors: Ganiyu A. Jimoh, St. Louis; Ronald J. Brinker, Ellisville, both of Mo.

[73] Assignee: Monsanto Company, St. Louis, Mo.

[21] Appl. No.: 09/249,406

[22] Filed: Feb. 12, 1999

Related U.S. Application Data

[60] Provisional application No. 60/074,577, Feb. 13, 1998.

[51] Int. Cl.$^7$ .............................. A01N 63/00; A01N 57/00
[52] U.S. Cl. ............................................. 504/118; 504/127
[58] Field of Search .................................... 504/116, 118, 504/127

[56] References Cited

U.S. PATENT DOCUMENTS

| | | | |
|---|---|---|---|
| 3,505,377 | 4/1970 | Morehouse | 260/448.2 |
| 3,799,758 | 3/1974 | Franz | 71/86 |
| 3,853,530 | 12/1974 | Franz | 71/76 |
| 4,140,513 | 2/1979 | Prill | 71/86 |
| 4,315,765 | 2/1982 | Large | 71/87 |
| 4,405,531 | 9/1983 | Franz | 260/501.12 |
| 4,481,026 | 11/1984 | Prisbylla | 71/86 |
| 4,507,250 | 3/1985 | Bakel | 260/502.5 F |
| 4,933,002 | 6/1990 | Petroff et al. | 71/116 |
| 5,389,680 | 2/1995 | Ruminski | 514/563 |
| 5,464,807 | 11/1995 | Claude et al. | 504/206 |

FOREIGN PATENT DOCUMENTS

| | | | |
|---|---|---|---|
| 658150 | 4/1992 | Australia | A01N 25/30 |
| 0 485 207 | 5/1992 | European Pat. Off. | A01N 25/04 |
| 0 535 596 | 4/1993 | European Pat. Off. | A01N 57/20 |
| 448538 | 1/1997 | European Pat. Off. | |
| WO 95/03881 | 2/1995 | WIPO | B01F 17/00 |
| WO 96/32839 | 10/1996 | WIPO | |

OTHER PUBLICATIONS

OSi Specialties, Inc.: Silwet® Surfactants (1994).
Stevens, P. J. G., *Pesticide Science* 38, 103–122 (1993).

Primary Examiner—Jose' G. Dees
Assistant Examiner—Alton Pryor
Attorney, Agent, or Firm—James C. Forbes

[57] ABSTRACT

A liquid composition is provided for application of a water-soluble exogenous chemical substance, such as the herbicide N-phosphonomethylglycine in the form of one or more salts thereof, to foliage of a plant, following dilution of the composition in water, to elicit a biological effect. The composition comprises a continuous aqueous phase having a discontinuous oil phase dispersed therein. The aqueous phase includes water wherein is dissolved the exogenous chemical substance in a biologically effective amount. The oil phase includes (a) an adjuvant amount of a siloxane surfactant of formula (I)

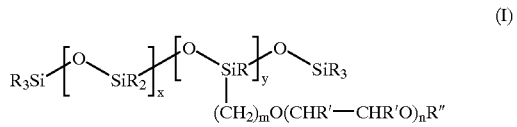

and (b) a substantially water-insoluble organic solvent for the siloxane surfactant. The organic solvent is present in an amount such that substantially all of the siloxane surfactant is contained in or associated with the oil phase. An advantage of the composition is that the siloxane surfactant exhibits much reduced hydrolytic breakdown by comparison with prior art compositions upon storage for extended periods.

18 Claims, No Drawings

STORAGE-STABLE COMPOSITION CONTAINING EXOGENOUS CHEMICAL SUBSTANCE AND SILOXANE SURFACTANT

This application claims the benefit of provisional application Ser. No. 60/074577 filed Feb. 13, 1998.

FIELD OF THE INVENTION

The present invention relates to compositions comprising an exogenous chemical substance which, upon dilution or dispersion in water, are useful for application to foliage of a plant to elicit biological activity in the plant.

The term "exogenous chemical substance" as used herein means a chemical substance, whether naturally or synthetically obtained, which is applied to a plant to result in expressing a desired biological activity. The term "biological activity" as used herein means elicitation of a stimulatory, inhibitory, regulatory, therapeutic, toxic or lethal response in the plant or in a pathogen, parasite or feeding organism present in or on the plant. Examples of exogenous chemical substances include, but are not limited to, chemical pesticides (such as herbicides, algicides, fungicides, bactericides, viricides, insecticides, miticides, nematicides and molluscicides), plant growth regulators, fertilizers and nutrients, gametocides, defoliants, desiccants, mixtures thereof and the like.

BACKGROUND OF THE INVENTION

For many purposes in agriculture and related endeavors it is desired to treat plants with exogenous chemical substances of various kinds. Many exogenous chemical substances are applied to foliage (i.e., leaves and other non-woody above-ground parts) of a plant, and have a site of action in the plant either close to or remote from the locus of application. Such substances are referred to herein as foliar-applied exogenous chemical substances.

Typically, when an exogenous chemical substance is applied to foliage by plant treatment processes known in the art, only a small portion of the amount applied reaches sites of action in the plant where a desired biological activity of the exogenous chemical substance can be usefully expressed. It is therefore a major desideratum in agriculture and related endeavors to enhance the efficiency of delivery of foliar-applied exogenous chemical substances to their sites of action in plants, and thereby to enhance the biological effectiveness of the exogenous chemical substance for the purpose for which the exogenous chemical substance is used.

Application to foliage of an exogenous chemical substance by processes known in the art does not universally result in inefficient delivery to sites of action. In some situations such processes provide excellent biological effectiveness, even at a low use rate of the exogenous chemical substance. In other situations the same processes, using the same rate of the exogenous chemical substance, provide inadequate biological effectiveness. Thus, these processes are inconsistent in the result they provide, or they cannot be relied upon to provide the desired result.

A problem is that it is seldom possible to identify in advance those situations where good biological effectiveness will be obtained, partly because so many factors influence efficiency of delivery. These factors include weather (temperature, relative humidity, daylength, cloudiness, precipitation, wind, etc.) preceding, during and following application, soil conditions (fertility, aeration, etc.), plant growth stage, health and physiological status, equipment-related inaccuracies in application, and other factors. Therefore, to help ensure reliable or consistent biological effectiveness of a foliar-applied exogenous chemical substance, the user typically applies the substance at a higher rate than truly necessary in the majority of situations.

Variability in biological effectiveness in field conditions is an especially troublesome problem in the case of exogenous chemical substances that are acids, and are typically formulated as water-soluble salts in which the exogenous chemical substance is present in an anionic form. Sometimes by converting such acid substances to esters, this variability can be moderated; however, in many cases esters show reduced biological effectiveness, for example due to inadequate conversion back to the parent acid once inside the treated plant. There remains a strong need for enhanced biological effectiveness, and enhanced reliability of biological effectiveness, of foliar-applied exogenous chemical substances, particularly anionic exogenous chemical substances.

An "anionic exogenous chemical substance" herein is an exogenous chemical substance whose molecular structure includes one or more acid, or proton-donating, sites, and is therefore capable of forming an anion in the presence of a proton acceptor. The term embraces substances that are zwitterionic. In describing an exogenous chemical substance as "anionic" herein, it is not implied that the exogenous chemical substance is necessarily in anionic form or that it is dissociated.

Benefits of a process providing greater reliability of biological effectiveness include an ability to reduce rates of application of exogenous chemical substances without sacrificing consistency of biological effectiveness. Pressures felt by the agricultural industry to reduce pesticide, particularly herbicide, usage are well evidenced by symposia on the subject, such as that held in 1993 by the Weed Science Society of America and documented in *Weed Technology* 8, 331–386 (1994). Reduced use rates bring rewards not only environmentally but also economically, as the cost per unit area treated decreases.

Foliar-applied exogenous chemical substances have frequently been applied together with amphiphilic materials, particularly amphiphilic surface-active agents, otherwise known as surfactants. Surfactants can influence biological effectiveness of a foliar-applied exogenous chemical substance in numerous ways.

When a dilute aqueous composition of an exogenous chemical substance is applied to foliage by conventional hydraulic spraying, the presence of surfactant in the dilute aqueous composition can alter the size distribution of the spray droplets, typically increasing the percentage of spray volume in the form of small droplets and reducing the percentage of spray volume in the form of large droplets. As smaller droplets have lower momentum than larger droplets, these smaller droplets are less likely to rebound from a foliar surface and consequently are more likely to be retained on that surface. Spray retention can also be facilitated by adhesion between surfactant molecules in a spray droplet and the foliar surface, which in most plants is waxy and hydrophobic. This adhesion reduces not only rebound but also run-off of spray droplets from the foliar surface. Surfactants also tend to increase the area of contact between a spray droplet and a foliar surface, and in many cases enhance penetration of an exogenous chemical substance from the droplet into and through cuticles of leaves to reach internal leaf tissues.

A class of surfactant that has been of particular interest for enhancing delivery of foliar-applied exogenous chemical substances to the interior of plant foliage is characterized by a hydrophobic moiety comprising three or more silicon atoms linked by oxygen atoms to form a trisiloxane or polysiloxane group. Such surfactants, herein called "siloxane surfactants", are a subclass of organosilicone surfactants and are exemplified by o-methoxypolyethoxypropylheptamethyltrisiloxane, sold for example by the OSi group of Witco Corporation as Silwet® L-77.

Silwet® L-77 has been reported to enhance foliar absorption of a wide range of exogenous chemical substances, including the herbicide glyphosate, by plants, this enhancement having been attributed at least in part to infiltration of stomata and other microscopic apertures in the foliar surface. This enhanced absorption commonly leads to enhanced biological effectiveness. However, on some plant species, at least under certain conditions, such enhanced biological effectiveness is not exhibited; indeed the presence of Silwet® L-77 has been found in many cases to cause antagonism of biological effectiveness of an exogenous chemical substance. As used herein, "antagonism" refers to a decrease in biological (such as herbicidal) effectiveness of an exogenous chemical substance (such as a herbicide) when a material (such as Silwet® L-77) is used in combination with the exogenous chemical substance.

Particularly in the case of herbicides, the risk of antagonism provides a disincentive to use siloxane surfactants such as Silwet® L-77, because multiple weed species are typically treated in the same field and the surfactant is likely to prove antagonistic for at least some of the weed species present.

Another problem, well known in the art, that has discouraged extensive use of siloxane surfactants such as Silwet® L-77 is hydrolytic instability of the trisiloxane or polysiloxane moiety in an aqueous medium. Cleavage of silicon-oxygen bonds in the trisiloxane or polysiloxane moiety results in degradation products which are ineffective as stomatal infiltrants and ineffective in enhancing biological effectiveness of foliar-applied exogenous chemical substances. Although hydrolysis occurs in the dilute aqueous compositions prepared by the end-user for application to foliage, typically these compositions are prepared immediately before use and the time available for hydrolysis is correspondingly short. More significant is the problem of hydrolysis in an aqueous concentrate composition, which for commercial acceptability must have a shelf-life of several months to several years.

This is a particular problem with compositions comprising water-soluble exogenous chemical substances, because these substances are most conveniently and economically formulated as aqueous concentrates. Even more particularly, it is a problem with anionic exogenous chemical substances, as these are often formulated at pH<7, i.e., at acid pH, and at such pH levels hydrolysis of siloxane surfactants tends to be accelerated. For example, glyphosate is most typically formulated as a mono-salt which, in aqueous solution, gives a pH of around 4.

It would be a major advance in the art to provide a water-based concentrate composition of a water-soluble exogenous chemical substance such as a glyphosate salt containing a siloxane surfactant that is effective as a stomatal infiltrant, yet wherein the siloxane surfactant has acceptable long-term chemical stability.

Glyphosate (N-phosphonomethylglycine) in its strict sense is an acid compound, but the word "glyphosate" is herein used in a less restrictive sense, except where the context dictates otherwise, to encompass not only glyphosate acid but also salts, adducts and esters thereof, and compounds which are converted to glyphosate in plant tissues or which otherwise provide glyphosate ions. In most commercial formulations of glyphosate, the glyphosate is present as a water-soluble salt. In this respect, glyphosate is typical of most exogenous chemical substances that are acids or that form anions.

Herbicidal salts of glyphosate are disclosed, for example, in U.S. Pat. No. 3,799,758 to Franz, U.S. Pat. No. 3,853,530 to Franz, U.S. Pat. No. 4,140,513 to Prill, U.S. Pat. No. 4,315,765 to Large, U.S. Pat. No. 4,405,531 to Franz, U.S. Pat. No. 4,481,026 to Prisbylla and U.S. Pat. No. 4,507,250 to Bakel. In most of the salts disclosed, the counterion to glyphosate anion is a relatively low molecular weight, non-amphiphilic cation. Typical of such salts are alkali metal, for example sodium and potassium, salts; ammonium salt; and salts having an ammonium, sulfonium or sulfoxonium cation substituted with 1–3 organic groups containing in total 1–6 carbon atoms, for example dimethylammonium, isopropylammonium, ethanolammonium and trimethylsulfonium salts.

Commercial formulations of glyphosate salts include, for example, Roundup® brand, Accord® brand, Roundup® Ultra brand and Roundup® Xtra brand herbicides of Monsanto Company, which contain the isopropylammonium salt, Roundup® Dry brand and Rival® brand herbicides of Monsanto Company, which contain the ammonium salt, Roundup® Geoforce brand herbicide of Monsanto Company, which contains the sodium salt, and Touchdown® brand herbicide of Zeneca, which contains the trimethylsulfonium salt.

Australian Patent No. 658150 discloses liquid aqueous concentrate compositions comprising a salt of glyphosate, a silicone copolymer wetting agent exemplified by the siloxane surfactant Silwet® L-77, and an amphoteric surfactant.

SUMMARY OF THE INVENTION

There is now provided a liquid composition comprising a continuous aqueous phase having a discontinuous oil phase dispersed therein. The aqueous phase includes water wherein is dissolved a water-soluble exogenous chemical substance in an amount which is biologically effective when the composition is diluted in a suitable volume of water and applied to foliage of a plant. The oil phase includes (a) an adjuvant amount of a siloxane surfactant of formula (I)

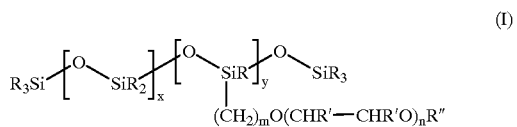

(I)

where x is an integer or average of integers of 0 to about 100, y is an integer or average of integers of 1 to about 30, each m is independently an integer of 1 to about 20, each n is independently an integer of 1 to about 30, each R group is independently a hydrogen or $C_{1-6}$ hydrocarbyl group, each R' group is independently a hydrogen or $C_{1-4}$ alkyl group, and each R" group is independently a hydrogen $C_{1-20}$ hydrocarbyl or an acyl group; and (b) a substantially water-insoluble organic solvent for the siloxane surfactant. The organic solvent is present in an amount such that substantially all of the siloxane surfactant is contained in or associated with the oil phase.

By "an adjuvant amount" of a siloxane surfactant is meant an amount such that upon dilution of the composition in a suitable volume of water and application of the diluted composition to foliage of a plant, the composition exhibits enhanced biological effectiveness by comparison with an otherwise similar composition lacking the siloxane surfactant.

Preferably the siloxane surfactant is a micropore infiltrant, present in an amount such that upon dilution of the composition in a suitable volume of water for application of the diluted composition to foliage of a plant, an infiltrating effective concentration of the micropore infiltrant results. A "micropore infiltrant" as contemplated herein is an amphiphilic agent having the property that when dissolved or dispersed in an aqueous composition it permits the aqueous composition to infiltrate microscopic pores in a hydrophobic surface. This property can be tested by means of an in vitro assay described herein. An "infiltrating effective concentration" of a micropore infiltrant is a concentration which can be shown by the in vitro assay to permit infiltration of such microscopic pores.

The phrase "an organic solvent for the siloxane surfactant" refers to an organic solvent in which the siloxane surfactant is soluble or one which itself is soluble in the siloxane surfactant, such that a solution can be provided having a weight/weight ratio of organic solvent to siloxane surfactant in at least part of the range from about 10:1 to about 1:10. The organic solvent is substantially insoluble in water; preferably the organic solvent has a solubility in water not greater than about 0.1% by weight at 20° C.

In providing herein that "substantially all of the siloxane surfactant is contained in or associated with the oil phase", it is meant that by any technique commonly known in the art for separating an aqueous phase and an oil phase in order to determine the content of an ingredient in each phase, it can be demonstrated that at most only a very minor amount, for example about 5% or less, of the siloxane surfactant is present in the aqueous phase, unassociated with the oil phase. Such techniques include centrifugation, heating, filtration and, if the oil phase is not stably dispersed in the aqueous phase, simply permitting settling of the denser phase below the less dense phase.

DETAILED DESCRIPTION OF THE INVENTION

A liquid composition of the invention comprises a continuous aqueous phase having a discontinuous oil phase dispersed therein. Contemplated compositions are not necessarily physically stable over a long period of time. Indeed in some such compositions the oil phase remains dispersed in the aqueous phase only as a result of continuous agitation. This is especially true following dilution of the composition in water to provide a plant treatment composition suitable for application to foliage. Devices for applying plant treatment compositions to plants, for example agricultural sprayers, are commonly equipped with agitators to maintain homogeneous mixing of such compositions prior to and during application.

Preferred compositions are rendered physically stable, at least for short periods of time, by the presence of an emulsifying system. This emulsifying system can be adequate to stabilize the concentrate composition without necessarily being adequate upon dilution of the composition in water to stabilize the resulting plant treatment composition. More preferably, however, an emulsifying system is present in an amount sufficient to stabilize a diluted plant treatment composition. This means that the emulsifying system prevents substantial phase separation in normal agricultural use from the time the plant treatment composition is prepared, by dilution in water of a concentrate composition, to the time the plant treatment composition is applied to foliage, for example by spraying. Substantial phase separation is readily observable by the appearance of a distinct oily layer on the surface of the composition when the composition is permitted to stand without agitation during the time period indicated. Typically the time of application is within 24 hours of the time of preparation of the plant treatment composition; however emulsion compositions which exhibit phase separation in shorter periods than this, for example 1 hour or even less, can still be useful, especially when the application equipment permits good agitation of the plant treatment composition.

One embodiment of the invention is a liquid concentrate composition that is an emulsion comprising a water-soluble exogenous chemical substance and a siloxane surfactant, and having (a) an aqueous phase that includes water in which the water-soluble exogenous chemical substance is dissolved, (b) a substantially water-insoluble organic solvent for the siloxane surfactant in an amount such that substantially all of the siloxane surfactant is contained in or associated with the oil phase, and (c) a stabilizing amount of an emulsifying system having one or more emulsifiers. The amount of exogenous chemical substance is sufficient, upon dilution in a suitable volume of water to form a plant treatment composition for application to foliage, to provide a biologically effective amount of the exogenous chemical substance. The amount of water is sufficient to maintain the exogenous chemical substance in solution in the aqueous phase. The siloxane surfactant is present in an adjuvant amount as defined herein; in a preferred embodiment where the siloxane surfactant is a micropore infiltrant, it is present in an amount that, upon dilution of the composition in a suitable volume of water to form a plant treatment composition for application to foliage, provides an infiltrating effective concentration of thesiloxane surfactant.

In the case of a liquid concentrate composition of the invention, a "stabilizing amount" of the emulsifying system is an amount sufficient to prevent substantial phase separation of the composition for a period of at least about 30 days when the emulsion is stored at temperatures from about 10° C. to about 30° C. It is preferred that the emulsion show no substantial phase separation for a period of at least about 180 days under the above conditions, or for a period of at least about 30 days when stored at temperatures from about −10° C. to about 40° C.; it is particularly preferred that no substantial phase separation occur for a period of at least about 180 days at storage temperatures from about −10° C. to about 40° C.

Liquid concentrate compositions of the invention can be oil-in-water macroemulsions or microemulsions, water-in-oil emulsions or water-in-oil-in-water multiple emulsions. All types of concentrate formulation having characteristics of an emulsion, including suspoemulsions, are possible within the invention.

The siloxane surfactant present in the oil phase of a composition of the invention conforms to formula (I)

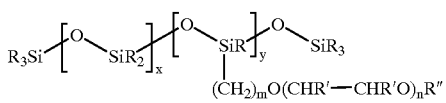

(I)

as described above. In preferred siloxane surfactants, x is an integer or average of integers of 0 to about 10, more preferably 0 or 1 and most preferably 0. In preferred siloxane surfactants, y is an integer or average of integers of 1 to about 10, most preferably 1. It is preferred that m be an integer of 2 to 6, most preferably 3. It is preferred that n be about 5 to about 20, with all R' groups being hydrogen. It is preferred that R groups be independently selected from hydrogen and $C_{1-4}$ alkyl groups, with hydrogen and methyl groups being particularly preferred. It is preferred that R" is a hydrogen or $C_{1-4}$ alkyl group, with hydrogen and methyl groups again being particularly preferred.

Siloxane surfactants of formula (I) are generally described in product literature of OSi Specialties, Inc. (e.g., "Silwet® Surfactants," OSi Specialties, Inc., Danbury, Conn., 1994), and in U.S. Pat. No. 3,505,377. Several polyoxyethylene trisiloxanes are available from OSi Specialties as Silwet® surface-active copolymers. Examples suitable as micropore infiltrants for the practice of the present invention include Silwet® L-77, Silwet® 408 and Silwet® 800. Another suitable micropore infiltrant is Sylgard® 309 of Dow Corning.

Micropore infiltrants of particular interest include those siloxane surfactants of formula (I) that are capable of reducing the surface tension of water to very low levels (typically below about 25 mN/m). In some cases a combination of two or more such surfactants, or a surfactant of formula (I) together with another surfactant, can provide especially strong micropore infiltrant properties in compositions of the invention.

When a siloxane surfactant is coformulated with glyphosate in a composition of the invention, the weight/weight ratio of siloxane surfactant to glyphosate acid equivalent is preferably in the range from about 1:20 to about 5:1, more preferably in the range from about 1:10 to about 1:1.

As indicated above, preferred siloxane surfactants are micropore infiltrants, that is, when dissolved or dispersed at a suitable concentration in water they form a solution or dispersion that infiltrates microscopic pores in a hydrophobic surface. For example, micropore infiltrants permit infiltration of a plant treatment composition into stomata or other openings in the surface of a plant leaf such as cracks or wounds, and ultimately into internal voids connected thereto. This property is referred to herein as "stomatal infiltration" and is believed to be at least in part responsible for providing the enhanced biological effectiveness characteristic of compositions of the present invention containing a micropore infiltrant.

The following test is one of several that can be useful in determining whether a siloxane surfactant of formula (I) can function as a micropore infiltrant in a composition of the present invention. Plants of a suitable test species are grown, for example in a greenhouse or growth chamber, to such a size that they have fully expanded leaves. Velvetleaf (*Abutilon theophrasti*) has been found to be a convenient species for this test, but other species having stomata on the upper surface of the leaves are similarly useful. Growing conditions immediately prior to the test should be such as to favor the fully expanded leaves having their stomata open; normally this means that the plants should have been exposed for at least one hour to a light intensity of at least about 475 microeinsteins, and that the plants should not be subject to physiological stress from excess or deficiency of water, from excessively high or low temperature, or from other adverse environmental conditions.

The procedure described herein relates to velvetleaf. Modifications may be found necessary or desirable if another species is chosen. A siloxane surfactant to be tested as a candidate micropore infiltrant is dissolved or dispersed in water at a desired concentration, and fluorescein is dissolved in the resulting liquid at 0.1% by volume. An automatic syringe is used to dispense 0.8 μl of the liquid containing fluorescein to each of three loci on the surface of one or more fully expanded leaves. The treated leaves remain attached to the plants throughout the procedure.

Exactly 10 minutes after dispensing the liquid, each treated leaf is washed with copious amounts of water (for example, at least 10 ml) to remove substantially all, i.e., all visually perceptible amount, of the fluorescein from the leaf surface. The plants are then removed to a darkened place where the treated leaves are observed with the naked eye under long-wave ultraviolet illumination. If fluorescence is observed at or close to the loci of deposition of the liquid, it can be concluded that the liquid has infiltrated stomata. The candidate siloxane surfactant present in such a liquid can be considered to be a micropore infiltrant. If desired, the degree of fluorescence can be quantified by appropriate instrumentation, but this is unnecessary if the objective is simply to know whether or not a candidate surfactant is a micropore infiltrant. Lack of observed fluorescence indicates no significant stomatal infiltration, in which case it can be concluded that the candidate siloxane surfactant is not a stomatal infiltrant.

To verify that plants are in suitable condition for the test, a known micropore infiltrant, such as the polyoxyethylene trisiloxane surfactant Silwet® L-77, can be tested by the above procedure. An aqueous solution of Silwet® L-77 at 0.05% by volume typically gives a weak fluorescence signal indicating that modest stomatal infiltration has occurred. An aqueous solution of Silwet® L-77 at 0.5% by volume typically gives a very strong fluorescence signal, indicating that a substantial amount of the solution has infiltrated stomata.

An alternative test for determining whether a candidate siloxane surfactant is a micropore infiltrant does not employ plants or other living material, and therefore has the major advantage that it is unaffected by the normal biological variability characteristic of in vivo assays such as the one described immediately above. This alternative test, described herein as an in vitro test or assay to reflect its non-use of living material, can be used to determine whether an aqueous solution or dispersion of a candidate siloxane surfactant is capable of penetrating or infiltrating microscopic pores in a hydrophobic surface, such as stomata of a leaf.

In the in vitro assay, the candidate surfactant can be dissolved or dispersed in water at any desired concentration, depending on the concentration to be used in the desired application. Suitable concentrations in water range, depending on the candidate surfactant, from about 0.1% to about 10% by weight, for example from about 0.25% to about 3% by weight.

A smooth solid substrate and an opaque membrane filter are selected having contrasting colors. Preferably the substrate is dark colored, for example black, and the membrane filter light colored or white. The membrane filter is composed of a hydrophobic material, preferably polytetrafluoroethylene (PTFE), and has a multiplicity of pores. Pore size of the membrane filter is selected to reflect the typical dimensions of pores which it is desired to infiltrate; for example in the case of a surfactant being tested as a potential stomatal infiltrant, a membrane filter should be selected having pores of diameter about 0.5 to about 2.5 μm, for example about 1 μm.

The selected membrane filter is placed on the substrate; in the case of a membrane filter having a smooth face and an opposing rough face, the membrane filter is placed with the smooth face adjacent to the substrate. One or more drops of an aqueous solution or dispersion of the candidate surfactant are then placed on the membrane filter. Any convenient drop size and number can be used; in the case of a PTFE membrane filter having 1 μm diameter pores, it has been found useful to apply 1–10, for example 3, drops each of 1–5 μl, for example 2 μl, volume. The drops are allowed to remain in contact with the surface of the membrane filter for a convenient length of time. The time for which the drops are allowed to remain on the filter depends on the application for which the test is being used and an optimum length of time can easily be determined without undue experimentation. In the present application, it has been found useful to leave the drops on the filter for a minimum of 1–30 minutes, for example a minimum of about 15 minutes.

At the end of this time, it can readily be seen if the liquid has permeated the pores of the membrane filter, because such permeation renders the membrane filter to some extent transparent, and the contrasting color of the substrate shows through the membrane filter. Permeation of the pores of the membrane filter in this test is a good predictive indication of penetration or infiltration of microscopic pores in the hydrophobic surface characteristic of the application of interest. For example, permeation of pores in a PTFE membrane filter having 1 μm porosity after a period of at least about 15 minutes is a good predictive indication of stomatal infiltration in plant leaves.

Particular test conditions which can be used to predict whether a siloxane surfactant of formula (I) is a useful micropore infiltrant are as follows. A solution or dispersion of the compound is prepared at a concentration of 0.5% by weight in deionized water. A black bottle cap (ca. 40 mm diameter) is placed on a solid surface such that the closed side of the bottle cap is down and the open, threaded side is up. A suitable PTFE membrane filter (47 mm diameter, 1.0 μm porosity, MSI brand, catalog no. F10P04700) has two faces: a smooth, shiny face and a rough, dull face. The filter is placed atop the cap so that the rough, dull face points upward. Three 2 μl drops of the solution or dispersion of the compound are applied to the rough, dull face of the PTFE membrane filter. The drops are allowed to stand on the filter for at least 15 minutes. During this time, it is noted whether the solution or dispersion has permeated the PTFE membrane filter. This can be determined visually because permeation causes the white filter to become transparent and the black bottle cap can be seen through the filter. If after 15 minutes no permeation has occurred, this is deemed a negative result and the test is terminated. A negative result indicates that the candidate surfactant is predicted not to be useful as a micropore infiltrant. If permeation has occurred within 15 minutes, this is deemed a positive result and the candidate surfactant is predicted to be a useful micropore infiltrant in a composition of the invention.

The oil phase of a composition of the invention comprises an organic solvent for the siloxane surfactant. A suitable organic solvent can be selected without undue experimentation on the basis of substantial insolubility or immiscibility of the organic solvent in water, and cosolubility of the siloxane surfactant and the organic solvent, i.e., the solubility of these two components in each other. The siloxane surfactant and the organic solvent must be sufficiently cosoluble to form, when mixed together, a solution having a weight/weight ratio of organic solvent to siloxane surfactant in at least part of the range from about 10:1 to about 1:10. Preferably the cosolubility of the siloxane surfactant and the organic solvent is sufficient to form a solution containing about 5 to about 10 parts by weight of the siloxane surfactant per part by weight of the organic solvent.

Organic solvents useful in compositions of the present invention preferably have a flash point above about 35° C., more preferably above about 90° C., and are preferably not antagonistic to the biological effectiveness of the exogenous chemical substance. Examples of suitable solvents include Solvesso™ Aromatic 100 and Aromatic 200, which are alkyl naphthalenic aromatic solvents available from Exxon, and Exxate™ 1000, an alkyl acetate with high solvency, also available from Exxon. Especially where the exogenous chemical substance is glyphosate, an aromatic solvent is particularly preferred.

The organic solvent is present in an amount such that substantially all of the siloxane surfactant is contained in or associated with the oil phase. Without being bound by theory, it is believed that the siloxane surfactant remains primarily in or associated with the oil phase not only because of the high solubility of the siloxane surfactant in the organic solvent but also because of the "salting out" effect of ions present in the aqueous phase. Ions present in the aqueous phase contributing to the "salting out" effect can include ions and counterions of the exogenous chemical substance, for example glyphosate anions and isopropylammonium cations where the exogenous chemical substance is the isopropylammonium salt of glyphosate, or they can be ions of other salts added to the formulation such as ammonium sulfate, sodium chloride, etc.

The aqueous phase of a composition of the invention comprises water having dissolved therein the selected exogenous chemical substance. Preferred exogenous chemical substances are acids or anionic compounds and are most usefully present in a composition of the invention in the form of one or more water-soluble salts. The aqueous phase can optionally contain, in addition to the exogenous chemical substance, other salts contributing to the ionic strength of the aqueous phase.

Water-soluble exogenous chemical substances which can usefully be applied in compositions of the present invention are normally, but not exclusively, those which have a beneficial effect on the overall growth or yield of desired plants such as crops, or a deleterious or lethal effect on the growth of undesirable plants such as weeds. A preferred group of such exogenous chemical substances are those that are normally applied post-emergence to the foliage of plants, i.e. foliar-applied exogenous chemical substances.

While the invention is not limited to any particular class of foliar-applied water-soluble exogenous chemical substance, it has been found to provide useful benefits for substances that rely at least in part for their biological effectiveness on systemic movement in plants. Systemic movement in plants can take place via apoplastic (non-living) pathways, including within xylem vessels and in intercellular spaces and cell walls, via symplastic (living) pathways, including within phloem elements and other tissues composed of cells connected sympastically by plasmodesmata, or via both apoplastic and symplastic pathways. For foliar-applied systemic exogenous chemical substances, the most important pathway is the phloem, and the present invention is believed to provide the greatest benefits for exogenous chemical substances that are phloem-mobile.

Compositions of the invention have proved particularly useful as herbicidal compositions, wherein the exogenous chemical substance is a foliar-applied herbicide, preferably a phloem-mobile foliar-applied herbicide. While it is likely that compositions of the present invention have the greatest applicability where the exogenous chemical substance is systemic, they can also be useful for non-systemic exogenous chemical substances such as the herbicide paraquat.

Preferred systemic exogenous chemical substances exist in the form of a salt comprising a biologically active ion and a counterion which is biologically inert or relatively inactive at the rates used. It is further preferred that such a salt has a molecular weight below about 300, excluding counterions. Especially suitable among such salts are herbicides, plant growth regulators and nematicides, in particular those having one or more of an amine, a carboxylic acid, a phosphonate or a phosphinate functional group in the biologically active ion. Among the most preferred of such salts are those having an amine group, a carboxylic acid group and a phosphonate or phosphinate group in the biologically active ion. Such especially preferred exogenous chemical substances include herbicides, for example glyphosate and glufosinate, plant growth regulators, for example ethephon, and nematicides, for example those disclosed in U.S. Pat. No. 5,389,680. Preferred nematicides of this group are salts of 3,4,4-trifluoro-3-butenoic acid or of N-(3,4,4-trifluoro-1-oxo-3-butenyl)glycine.

Illustratively herbicides that can be used in the method of the invention include acifluorfen, asulam, benazolin, bentazon, bialaphos, bromacil, bromoxynil, chloramben, clopyralid, 2,4-D, 2,4-DB, dalapon, dicamba, dichlorprop, diclofop, diquat, endothall, fenac, fenoxaprop, flamprop, fluazifop, flumiclorac, fluoroglycofen, fomesafen, fosamine, glufosinate, glyphosate, haloxyfop, imazameth, imazamethabenz, imazamox, imazapic, imazapyr, imazaquin, imazethapyr, ioxynil, MCPA, MCPB, mecoprop, methylarsonic acid, naptalam, nonanoic acid, paraquat, picloram, quinclorac, quizalofop, sulfamic acid, 2,3,6-TBA, TCA and triclopyr. Phloem-mobile herbicides that are preferred for use by the method of the invention include but are not limited to aminotriazole, asulam, bialaphos, clopyralid, dicamba, glufosinate, glyphosate, imidazolinones such as imazameth, imazamethabenz, imazamox, imazapic, imazapyr, imazaquin and imazethapyr, phenoxies such as 2,4-D, 2,4-DB, dichlorprop, MCPA, MCPB and mecoprop, picloram and triclopyr.

Herbicidally active derivatives of the above herbicides can also be used in compositions of the invention. A herbicidally active derivative is any compound which is a minor structural modification, most commonly but not restrictively a salt or ester, of a herbicide, said compound retaining the essential activity of the parent herbicide although not necessarily having a potency equal to that of the parent herbicide. Usually but not always, the derivative converts to the parent herbicide before or after it enters the treated plant, and is analogous to a pro-drug that converts to an active drug in vivo. Mixtures or coformulations of a herbicide or herbicidally active derivative with other ingredients, or of more than one herbicide, are likewise within the scope contemplated by the present invention.

An especially preferred herbicide useful in a composition of the present invention is glyphosate, the acid form of which is alternatively known as N-phosphonomethylglycine. Illustratively, glyphosate salts useful herein are disclosed in U.S. Pat. Nos. 3,799,758 and No. 4,405,531. Glyphosate salts that can be used according to the present invention include but are not restricted to alkali metal, for example sodium and potassium, salts; ammonium salt; $C_{1-16}$ alkylammonium, for example dimethylammonium and isopropylammonium, salts; $C_{1-16}$ alkanolammonium, for example monoethanolammonium, salt; $C_{1-16}$ alkylsulfonium, for example trimethylsulfonium, salts; mixtures thereof and the like. The N-phosphonomethylglycine molecule has three acid sites having different pKa values; accordingly mono-, di- and tribasic salts, or any mixture thereof, or salts of any intermediate level of neutralization, can be used.

Glyphosate salts are commercially significant in part because they are water soluble. Many ammonium, alkylammonium, alkanolammonium, alkylsulfonium and alkali metal salts are highly water soluble, allowing for formulation as highly concentrated aqueous solutions which can be diluted in water at the point of use. The present invention encompasses concentrate compositions comprising an aqueous phase containing a glyphosate salt in aqueous solution, and an oil phase having contained therein or associated therewith an appropriate amount of a micropore infiltrant, so that on application to plant foliage, following dilution in water, both glyphosate and the micropore infiltrant are deposited on the foliage.

Contemplated liquid concentrate compositions of glyphosate can contain from about 50 to about 500 grams per liter of glyphosate, expressed as acid equivalent (g a.e./l). Higher glyphosate concentrations, for example from about 300 to about 500 g a.e./l, are preferred.

Emulsifying systems appropriate for stabilizing a dispersion of an organic solvent in a salt-containing aqueous phase, as required in certain embodiments of the present invention, are readily selected without undue experimentation by those of ordinary skill in the art. So long as the emulsifying system provides good stability, selection of a specific emulsifying system has not been found to be critical to the biological effectiveness of the resulting emulsion. Illustrative emulsifying systems are disclosed in the Examples herein.

Compositions of the invention can optionally contain, in addition to an exogenous chemical substance, an organic solvent and a siloxane surfactant, any other desired agriculturally acceptable ingredients. Especially useful ingredients, at least in the case of glyphosate compositions, are surfactants additional to the siloxane surfactant, and herein referred to as "cosurfactants". Cosurfactants have various functions. For example, they assist in retention of aqueous spray solutions on the relatively hydrophobic surfaces of plant leaves, as well as helping the glyphosate to penetrate the waxy outer layer (cuticle) of the leaf and thereby contact living tissues within the leaf. Cosurfactants can perform other useful functions as well, including serving as emulsifiers to permit the organic solvent and siloxane surfactant to be incorporated in a stable homogeneous formulation, as indicated above.

There is no restriction in the type or chemical class of cosurfactant that can be used in compositions of the invention. Nonionic, anionic, cationic and amphoteric types, or combinations of more than one of these types, are all useful in particular situations. For glyphosate compositions, however, it is generally preferred that at least one of the cosurfactants, if any, present should be other than anionic.

Among anionic surfactants, especially preferred classes include fatty acids; alkyl-substituted benzene sulfonates and diphenylether disulfonates; naphthalene sulfonates; acyl isethionates, sarcosinates, sulfosuccinates, semisulfosuccinates, sulfosuccinamates and taurates; alkane and α-olefin sulfonates; sulfates and sulfonates of oils and fatty esters; sulfates, sulfonates, and phosphate mono- and diesters of alcohols, alkylphenols, polyoxyethylene alcohols and polyoxyethylene alkylphenols; and carboxylates of polyoxyethylene alcohols and polyoxyethylene alkylphenols. These can be used in their acid form or as salts, for example sodium, potassium or ammonium salts.

Among cationic surfactants, especially preferred classes include polyoxyethylene tertiary alkylamines or alkenylamines, such as ethoxylated fatty amines, quaternary ammonium surfactants and polyoxyethylene alkyletheramines. Representative specific examples of such cationic surfactants include polyoxyethylene (5) cocoamine, polyoxyethylene (15) tallowamine, distearyldimethylammonium chloride, N-dodecylpyridine chloride and polyoxypropylene (8) oxyethylene trimethylammonium chloride. Particularly preferred polyoxyethylene alkyletheramines are those disclosed in International Publication No. WO 96/32839.

Many cationic quaternary ammonium surfactants of diverse structures are known in the art to be useful in combination with glyphosate and other exogenous chemical substances and can be used in compositions contemplated herein; such quaternary ammonium surfactants have formula (VII):

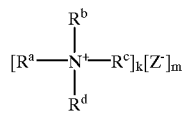

(VII)

where $Z^-$ is a suitable anion such as chloride, bromide, iodide, acetate, salicylate, sulfate or phosphate; k and m are integers such that the positive electrical charges on cations balance the negative electrical charges on anions; and options for $R^a$, $R^b$, $R^c$ and $R^d$ include, without limitation, the following:

(i) $R^a$ is a benzyl or $C_{8-24}$, preferably a $C_{12-18}$, alkyl or alkenyl group, and $R^b$, $R^c$ and $R^d$ are independently $C_{1-4}$ alkyl, preferably methyl, groups;

(ii) $R^a$ and $R^b$ are independently $C_{8-24}$, preferably $C_{12-18}$, alkyl or alkenyl groups, and $R^c$ and $R^d$ are independently $C_{1-4}$ alkyl, preferably methyl, groups;

(iii) $R^a$ is a $C_{8-24}$, preferably a $C_{12-18}$, alkyl or alkenyl group, $R^b$ is a polyoxyalkylene chain having about 2 to about 100 $C_{2-4}$ alkylene oxide units, preferably ethylene oxide units, and $R^c$ and $R^d$ are independently $C_{1-4}$ alkyl, preferably methyl, groups;

(iv) $R^a$ is a $C_{8-24}$, preferably a $C_{12-18}$, alkyl or alkenyl group, $R^b$ and $R^c$ are polyoxyalkylene chains having in total about 2 to about 100 $C_{2-4}$ alkylene oxide units, preferably ethylene oxide units, and $R^d$ is a $C_{1-4}$ alkyl, preferably a methyl, group; or (v) $R^a$ is a polyoxyalkylene chain having about 2 to about 100 $C_{2-4}$ alkylene oxide units in which $C_{3-4}$ alkylene oxide units, preferably propylene oxide units, predominate, and $R^b$, $R^c$ and $R^d$ are independently $C_{1-4}$ alkyl, preferably methyl or ethyl, groups. Particularly preferred quaternary ammonium surfactants of this type are those disclosed in U.S. Pat. No. 5,464,807.

In a preferred embodiment of the present invention, an amphiphilic quaternary ammonium compound, or mixture of such compounds, is present, having formula (VIII):

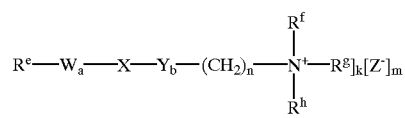

(VIII)

wherein $R^e$ is a hydrocarbyl or haloalkyl group having about 6 to about 22 carbon atoms; W and Y are independently O or NH; a and b are independently 0 or 1 but at least one of a and b is 1; X is CO, SO or $SO_2$; n is 2 to 4; $R^f$, $R^g$ and $R^h$ are independently $C_{1-4}$ alkyl; and k, m and $Z^-$ have the same meanings as in formula (VII). $R^e$ in one particular embodiment is a hydrocarbyl group having about 12 to about 18 carbon atoms. $R^e$ can also be fluorinated. In one specific embodiment, $R^e$ is perfluorinated, and preferably has about 6 to about 12 carbon atoms. In one particularly preferred embodiment, $R^e$ is a saturated perfluoroalkyl group having about 6 to about 12 carbon atoms, X is CO or $SO_2$, Y is NH, a is 0, b is 1, n is 3, $R^f$, $R^g$ and $R^h$ are methyl groups, k and m are each 1, and $Z^-$ is a chloride, bromide or iodide anion.

Sulfonylamino compounds of formula (VIII), i.e., those wherein X is $SO_2$, Y is NH, a is 0 and b is 1, are especially preferred. Suitable examples include 3-(((heptadecafluorooctyl)sulfonyl)amino)-N,N,N-trimethyl-1-propaminium iodide, available for example as Fluorad™ FC-135 from 3M Company, and the corresponding chloride. It is believed that Fluorad™ FC-754 of 3M Company comprises the corresponding chloride.

Among nonionic surfactants, especially preferred classes include polyoxyethylene alkyl, alkenyl or alkylaryl ethers, such as polyoxyethylene primary or secondary alcohols, alkylphenols or acetylenic diols; polyoxyethylene alkyl or alkenyl esters, such as ethoxylated fatty acids; sorbitan alkylesters, whether ethoxylated or not; glyceryl alkylesters; sucrose esters; and alkyl polyglycosides. Representative specific examples of such nonionic surfactants include polyoxyethylene (9) nonylphenol, Neodol™ 25-7 of Shell (a polyoxyethylene (7) $C_{12-15}$ linear primary alcohol), Plurafac™ A-38 of BASF (a polyoxyethylene (27) $C_{16-18}$ linear primary alcohol), Tergitol™ 15-S-9 of Union Carbide (a polyoxyethylene (9) $C_{12-15}$ secondary alcohol), Tween™ 20 of ICI (a polyoxyethylene (20) sorbitan monolaurate), Surfynol™ 465 of Air Products (a polyoxyethylene (10) 2,4,7,9-tetramethyl-5-decyne-4,7-diol) and Agrimul™ PG-2069 of Henkel (a $C_{9-11}$ alkyl polyglucoside).

Among amphoteric cosurfactants, especially preferred classes include polyoxyalkylene alkylamine oxides, alkylbetaines, alkyl-substituted amino acids and the like.

Hydrophobic moieties of cosurfactants useful in compositions of the invention can be essentially hydrocarbon based, or can contain silicon atoms, for example in the form of siloxane groups, or fluorine atoms, for example as partially fluorinated alkyl or perfluoroalkyl groups. Hydrocarbon chains of cosurfactants useful herein typically have from about 8 to about 20, preferably from about 12 to about 18, carbon atoms, and are branched or unbranched, saturated or unsaturated. Polyoxyalkylene moieties of cosurfactants useful in compositions of the invention are preferably polyoxyethylene or polyoxyethylene-polyoxypropylene chains.

Standard reference sources from which one of skill in the art can select suitable cosurfactants, without limitation to the above mentioned classes, include *Handbook of Industrial Surfactants,* Second Edition (1997) published by Gower, *McCutcheon's Emulsifiers and Detergents,* North American and International Editions (1997) published by MC Publishing Company, and *International Cosmetic Ingredient Dictionary*, Sixth Edition (1995) Volumes 1 and 2, published by the Cosmetic, Toiletry and Fragrance Association.

Other optional components of compositions of the invention include agents to modify color, viscosity, gelling properties, freezing point, hygroscopicity, caking behavior, dissolution rate, dispersibility, or other formulation characteristics.

A second exogenous chemical substance can optionally be included. This can be a water-soluble salt of an acid or anionic exogenous chemical substance, selected for example from those hereinbefore listed. Alternatively or in addition, an exogenous chemical substance that is other than acid or anionic can be included.

For example, a glyphosate composition of the invention can optionally contain, in addition to glyphosate, an anionic herbicidal compound such as acifluorfen, asulam, benazolin, bentazon, bialaphos, clopyralid, 2,4-D, 2,4-DB, dalapon, dicamba, dichlorprop, diclofop, fenoxaprop, flamprop, fluazifop, fluoroglycofen, fluroxypyr, fomesafen, fosamine, glufosinate, haloxyfop, imazameth, imazamethabenz, imazamox, imazapic, imazapyr, imazaquin, imazethapyr, MCPA, MCPB, mecoprop, methylarsonic acid, nonanoic acid, picloram, sulfamic acid, 2,3,6-TBA, TCA or triclopyr. Such additional anionic compound is present as one or more salts. Similarly, a composition of the invention containing salts of an anionic herbicide can optionally contain a herbicidal compound that is other than anionic, such as for example an ester derivative of an anionic herbicide, or a herbicide selected from acetochlor, aclonifen, alachlor, ametryn, amidosulfuron, anilofos, atrazine, azafenidin, azimsulfuron, benfluralin, benfuresate, bensulfuron-methyl, bensulide, benzofenap, bifenox, bromobutide, bromofenoxim, butachlor, butamifos, butralin, butroxydim, butylate, cafenstrole, carbetamide, carfentrazone-ethyl, chlomethoxyfen, chlorbromuron, chloridazon, chlorimuron-ethyl, chlorotoluron, chlornitrofen, chlorotoluron, chlorpropham, chlorsulfuron, chlorthal-dimethyl, chlorthiamid, cinmethylin, cinosulfuron, clethodim, clodinafop-propargyl, clomazone, clomeprop, cloransulam-methyl, cyanazine, cycloate, cyclosulfamuron, cycloxydim, cyhalofop-butyl, daimuron, desmedipham, desmetryn, dichlobenil, diclofop-methyl, diflufenican, dimefuron, dimepiperate, dimethachlor, dimethametryn, dimethenamid, dinitramine, dinoterb, diphenamid, dithiopyr, diuron, EPTC, esprocarb, ethalfluralin, ethametsulfuron-methyl, ethofumesate, ethoxysulfuron, etobenzanid, fenoxaprop-ethyl, fenuron, flamprop-methyl, flazasulfuron, fluazifop-butyl, fluchloralin, flumetsulam, flumiclorac-pentyl, flumioxazin, fluometuron, fluorochloridone, fluoroglycofen-ethyl, flupoxam, flurenol, fluridone, fluroxypyr-1-methylheptyl, flurtamone, fluthiacet-methyl, fomesafen, halosulfuron, haloxyfop-methyl, hexazinone, imazosulfuron, indanofan, isoproturon, isouron, isoxaben, isoxaflutole, isoxapyrifop, lactofen, lenacil, linuron, mefenacet, metamitron, metazachlor, methabenzthiazuron, methyldymron, metobenzuron, metobromuron, metolachlor, metosulam, metoxuron, metribuzin, metsulfuron, molinate, monolinuron, naproanilide, napropamide, naptalam, neburon, nicosulfuron, norflurazon, orbencarb, oryzalin, oxadiargyl, oxadiazon, oxasulfuron, oxyfluorfen, pebulate, pendimethalin, pentanochlor, pentoxazone, phenmedipham, piperophos, pretilachlor, primisulfuron, prodiamine, prometon, prometryn, propachlor, propanil, propaquizafop, propazine, propham, propisochlor, propyzamide, prosulfocarb, prosulfuron, pyraflufen-ethyl, pyrazolynate, pyrazosulfuron-ethyl, pyrazoxyfen, pyributicarb, pyridate, pyriminobac-methyl, quinclorac, quinmerac, quizalofop-ethyl, rimsulfuron, sethoxydim, siduron, simazine, simetryn, sulcotrione, sulfentrazone, sulfometuron, sulfosulfuron, tebutam, tebuthiuron, terbacil, terbumeton, terbuthylazine, terbutryn, thenylchlor, thiazopyr, thifensulfuron, thiobencarb, tiocarbazil, tralkoxydim, triallate, triasulfuron, tribenuron, trietazine, trifluralin, triflusulfuron and vernolate.

Exogenous chemical substances useful in compositions of the invention can be selected from those listed in standard reference works such as *The Pesticide Manual*, 11th Edition, British Crop Protection Council (1997), and *Farm Chemicals Handbook* '97, Meister Publishing Company (1997).

A process of preparing a composition of the invention comprises mixing the various ingredients in a suitable vessel. A presently preferred order of addition of the ingredients is as follows. First, all required emulsifiers are added to a concentrated aqueous solution of the exogenous chemical substance to form a first mixture. The siloxane surfactant is added to the organic solvent with agitation to form a second mixture. The second mixture is then added to the first mixture with agitation to form the finished composition.

An alternative order of addition is as follows. A hydrophilic emulsifier is added to a concentrated aqueous solution of the exogenous chemical substance with agitation to form a first mixture. The siloxane surfactant and a lipophilic emulsifier are added to the organic solvent with agitation to form a second mixture. The second mixture is added to the first mixture with agitation to form the finished composition.

The selection of application rates for a composition of the invention containing a specific exogenous chemical substance in order to provide a desired level of biological activity is within the skill of the ordinary agricultural technician. One of skill in the art will recognize that individual plant conditions, weather and growing conditions, as well as the specific exogenous chemical substance selected, can affect the results achieved in using a composition of the present invention. Where the exogenous chemical substance is glyphosate, much information is available in published literature about appropriate application rates. Over two decades of glyphosate use and published studies relating to such use have provided abundant information from which a weed control practitioner can select glyphosate application rates that are herbicidally effective on particular species at particular growth stages in particular environmental conditions. Generally, preferred application rates for glyphosate are from about 100 to about 2500 g a.e./ha, more preferably from about 250 to about 1500 g a.e./ha.

The method of the present invention where the exogenous chemical substance is glyphosate, more particularly a water-soluble glyphosate salt, is applicable to any and all plant species on which glyphosate is biologically effective as a herbicide or plant growth regulator. This encompasses a very wide variety of plant species worldwide. Likewise, compositions of the invention containing glyphosate can be applied to any and all plant species on which glyphosate is biologically effective.

Herbicidal compositions of glyphosate or derivatives thereof are used to control a very wide variety of plants worldwide. Glyphosate compositions of the invention can be applied to a plant in a herbicidally effective amount, and can effectively control one or more plant species of one or more of the following genera without restriction: Abutilon, Amaranthus, Artemisia, Asclepias, Avena, Axonopus, Borreria, Brachiaria, Brassica, Bromus, Chenopodium, Cirsium, Commelina, Convolvulus, Cynodon, Cyperus, Digitaria, Echinochloa, Eleusine, Elymus, Equisetum, Erodium, Helianthus, Imperata, Ipomoea, Kochia, Lolium, Malva, Oryza, Ottochloa, Panicum, Paspalum, Phalaris, Phragmites, Polygonum, Portulaca, Pteridium, Pueraria, Rubus, Salsola, Setaria, Sida, Sinapis, Sorghum, Triticum, Typha, Ulex, Xanthium and Zea.

Particularly important annual broadleaf species for which glyphosate compositions are used are exemplified without limitation by the following: velvetleaf (*Abutilon theophrasti*), pigweed (Amaranthus spp.), buttonweed (Borreria spp.), oilseed rape, canola, indian mustard, etc. (Brassica spp.), commelina (Commelina spp.), filaree (Erodium spp.), sunflower (Helianthus spp.), morningglory (Ipomoea spp.), kochia (*Kochia scoparia*), mallow (Malva spp.), wild buckwheat, smartweed, etc. (Polygonum spp.), purslane (Portulaca spp.), russian thistle (Salsola spp.), sida (Sida spp.), wild mustard (*Sinapis arvensis*) and cocklebur (Xanthium spp.)

Particularly important annual narrowleaf species for which glyphosate compositions are used are exemplified without limitation by the following: wild oat (*Avena fatua*), carpetgrass (Axonopus spp.), downy brome (*Bromus tectorum*), crabgrass (Digitaria spp.), barnyardgrass (*Echinochloa crus-galli*), goosegrass (*Eleusine indica*), annual ryegrass (*Lolium multiflorum*), rice (*Oryza sativa*), ottochloa (*Ottochloa nodosa*), bahiagrass (*Paspalum notatum*), canarygrass (Phalaris spp.), foxtail (Setaria spp.), wheat (*Triticum aestivum*) and corn (*Zea mays*).

Particularly important perennial broadleaf species for which glyphosate compositions are used are exemplified without limitation by the following: mugwort (Artemisia spp.), milkweed (Asclepias spp.), canada thistle (*Cirsium arvense*), field bindweed (*Convolvulus arvensis*) and kudzu (Pueraria spp.).

Particularly important perennial narrowleaf species for which glyphosate compositions are used are exemplified without limitation by the following: brachiaria (Brachiaria spp.), bermudagrass (*Cynodon dactylon*), yellow nutsedge (*Cyperus esculentus*), purple nutsedge (*C. rotundus*), quackgrass (*Elymus repens*), lalang (*Imperata cylindrica*), perennial ryegrass (*Lolium perenne*), guineagrass (*Panicum maximum*), dallisgrass (*Paspalum dilatatum*), reed (Phragmites spp.), johnsongrass (*Sorghum halepense*) and cattail (Typha spp.).

Other particularly important perennial species for which glyphosate compositions are used are exemplified without limitation by the following: horsetail (Equisetum spp.), bracken (*Pteridium aquilinum*), blackberry (Rubus spp.) and gorse (*Ulex europaeus*).

Thus, glyphosate compositions of the present invention, and a process for treating plants with such compositions, can be useful on any of the above species. In a particular contemplated process, a plant treatment composition of the invention comprising glyphosate is applied to foliage of crop plants genetically transformed to tolerate glyphosate, and simultaneously to foliage of weeds or undesired plants growing in close proximity to such crop plants. This process results in control of the weeds or undesired plants while leaving the crop plants substantially unharmed. Crop plants genetically transformed to tolerate glyphosate include those whose seeds are sold by Monsanto or under license from Monsanto bearing the Roundup Ready® trademark. These include varieties of cotton, soybean, canola and corn.

Application of plant treatment compositions to foliage of plants is preferably accomplished by spraying, using any conventional means for spraying liquids, such as spray nozzles or spinning-disk atomizers. Compositions of the present invention can be used in precision farming techniques, in which apparatus is employed to vary the amount of exogenous chemical substance applied to different parts of a field, depending on variables such as the particular plant species present, plant growth stage, soil moisture status, etc. In one embodiment of such techniques, a global positioning system operated with the spraying apparatus can be used to apply the desired amount of the composition to different parts of a field.

A plant treatment composition is preferably dilute enough to be readily sprayed using standard agricultural spray equipment. Suitable application rates for the present invention vary depending upon such factors as the type and concentration of active ingredient and the plant species involved. Useful rates for applying an aqueous composition to a field of foliage can range from about 25 to about 1,000 liters per hectare (l/ha), preferably about 50 to about 300 l/ha, by spray application.

EXAMPLES

The following examples are provided for illustrative purposes only and are not intended to limit the scope of the present invention. In these examples, percentage amounts refer to percent by weight unless otherwise noted.

Certain glyphosate formulations were used in the following examples for comparative purposes. They included:

Formulation J: which consists of 41% by weight of glyphosate IPA salt in aqueous solution, together with surfactant. This formulation is sold in the USA by Monsanto Company under the ROUNDUP® ULTRA trademark. Formulation J contains 356 grams of glyphosate acid equivalent per liter (g a.e./l).

Formulation L: which consists of 62% by weight of glyphosate IPA salt in aqueous solution, with no surfactant. This formulation is available from Monsanto Company as MON 0139. Formulation L contains 570 g a.e./l of glyphosate.

Other formulations used are described in the particular Examples where they occur.

Example 1

Compositions 1-1 to 1-9 and 1-12 to 1-46 comprising the IPA salt of glyphosate were prepared, having the ingredients shown in Table 1. There are no compositions 1-10 or 1-11. Generally these compositions were prepared as follows.

First, all required emulsifiers were added to a 62% aqueous solution of IPA glyphosate with agitation to form a first mixture. Silwet® L-77 was added to the organic solvent with agitation to form a second mixture. The second mixture was then added to the first mixture with agitation to form the finished composition.

The following emulsifiers were used. Agrimul™ PG 2069 is a $C_{9-11}$ alkyl 1.5 polyglucoside of Henkel. Pluronic™ P-103 is an ethylene oxide propylene oxide block copolymer of BASF. Span™ 40 is a sorbitan monopalmitate of ICI. Span™ 65 is a sorbitan tristearate of ICI. Span™ 85 is a sorbitan trioleate of ICI. Stepfac™ 8171 is a phosphate ester of polyoxyethylene nonylphenol of Stepan. Toximul™ TANS-5 is a polyoxyethylene tallowamine salt of an alkylphenol ether sulfate of Stepan. Tryfac™ 5552 is a phosphate ester of polyoxyethylene decanol of Henkel. Variquat™ 638 is a methyl bis(2-hydroxyethyl) cocoammonium chloride, with isopropanol as solvent, of Witco. Variquat™ 638 PG is similar except with propylene glycol as solvent in place of isopropanol. Certain compositions of the Examples contained a blend of two nonionic emulsifiers, a butyl ethylene oxide propylene oxide copolymer and a polyoxyethylene 20 sorbitan tritallate, as indicated in Table 1 by "nonionic blend".

In compositions 1-27, 1-31, and 1-33, the pH of the aqueous phase was adjusted to approximately 7 prior to mixing with the organic phase. In the case of composition 1-27, this was done by adding potassium hydroxide. In the case of compositions 1-31 and 1-33, this was done by adding isopropylamine.

TABLE 1

| Composition | Glyph-osate a.e. % | Silwet ® L-77 % | Organic solvent name | % | Emulsifier #1 name | % | Emulsifier #2 name | % |
|---|---|---|---|---|---|---|---|---|
| 1-1 | 36.8 | none | Aromatic 200 | 17.7 | Agrimul PG 2069 | 0.9 | Span 85 | 0.9 |
| 1-2 | 36.8 | none | Exxate 1000 | 17.7 | Agrimul PG 2069 | 0.9 | Span 85 | 0.9 |
| 1-3 | 28.9 | 14.7 | Aromatic 200 | 17.7 | Agrimul PG 2069 | 0.9 | Span 85 | 0.9 |
| 1-4 | 36.8 | none | Aromatic 200 | 17.7 | Agrimul PG 2069 | 0.9 | Span 85 | 0.9 |
| 1-5 | 28.9 | 14.7 | Exxate 1000 | 17.7 | Agrimul PG 2069 | 0.9 | Span 85 | 0.9 |
| 1-6 | 36.8 | none | Exxate 1000 | 17.7 | Agrimul PG 2069 | 0.9 | Span 85 | 0.9 |
| 1-7 | 33.9 | 17.2 | Aromatic 200 | 7.9 | Agrimul PG 2069 | 0.8 | none | |
| 1-8 | 33.9 | 17.2 | Aromatic 200 | 7.9 | none | | Span 85 | 0.8 |
| 1-9 | 34.1 | 17.3 | Aromatic 200 | 8.0 | none | | none | |
| 1-12 | 35.5 | 17.9 | Aromatic 200 | 2.8 | Toximul TANS-5 | 0.8 | nonionic blend | 0.7 |
| 1-13 | 35.5 | 17.9 | Exxate 1000 | 2.8 | Toximul TANS-5 | 0.8 | nonionic blend | 0.7 |
| 1-14 | 34.3 | 17.4 | Exxate 1000 | 2.7 | Toximul TANS-5 | 1.9 | nonionic blend | 2.9 |
| 1-15 | 30.0 | 15.0 | Aromatic 200 | 17.6 | Agrimul PG 2069 | 0.9 | Span 85 | 0.9 |
| 1-16 | 32.9 | 16.6 | Aromatic 200 | 9.6 | Agrimul PG 2069 | 1.0 | Span 85 | 1.0 |
| 1-17 | 34.4 | 17.4 | Aromatic 200 | 5.3 | Agrimul PG 2069 | 1.0 | Span 85 | 1.0 |
| 1-18 | 34.7 | 17.8 | Aromatic 200 | 2.9 | Agrimul PG 2069 | 1.7 | nonionic blend Stepfac 8171 | 0.3 1.4 |
| 1-19 | 34.9 | 18.7 | Aromatic 200 | 2.8 | Agrimul PG 2069 | 1.2 | Stepfac 8171 | 1.2 |
| 1-20 | 35.3 | 18.4 | Aromatic 200 | 2.9 | Toximul TANS-5 | 0.7 | nonionic blend | 0.7 |
| 1-21 | 35.8 | 17.4 | Aromatic 200 | 2.7 | Agrimul PG 2069 | 0.8 | Span 40 Pluronic P-103 | 0.5 0.5 |
| 1-22 | 35.6 | 17.9 | Aromatic 200 | 2.7 | Agrimul PG 2069 | 1.0 | Tryfac 5552 | 0.6 |
| 1-23 | 34.7 | 17.6 | Aromatic 200 | 2.6 | Agrimul PG 2069 | 2.0 | Tryfac 5552 | 1.9 |
| 1-24 | 36.1 | 17.6 | Exxate 1000 | 2.6 | none | | cetyl alcohol | 0.7 |
| 1-25 | 36.2 | 17.3 | Exxate 1000 | 2.7 | none | | Span 65 | 0.7 |
| 1-26 | 29.0 | 14.4 | Aromatic 100 | 20.0 | Variquat 638 | 2.0 | none | |
| 1-27 | 27.0 | 14.4 | Aromatic 100 | 20.0 | Variquat 638 | 2.0 | none | |
| 1-28 | 34.0 | none | Aromatic 100 | 23.0 | Variquat 638 | 2.0 | none | |
| 1-29 | 29.0 | 14.4 | Aromatic 100 | 20.0 | Variquat 638 | 2.0 | none | |
| 1-30 | 29.0 | 14.4 | Aromatic 100 | 20.0 | Variquat 638 PG | 2.0 | none | |
| 1-31 | 27.0 | 14.4 | Aromatic 100 | 20.0 | Variquat 638 | 2.0 | none | |
| 1-32 | 29.0 | 14.4 | Aromatic 200 | 20.0 | Variquat 638 | 2.0 | none | |
| 1-33 | 27.0 | 14.4 | Aromatic 200 | 20.0 | Variquat 638 | 2.0 | none | |
| 1-34 | 34.0 | 19.6 | Aromatic 100 | 3.0 | Variquat 638 Toximul TANS-5 | 1.0 0.8 | nonionic blend | 0.7 |
| 1-35 | 36.0 | 17.9 | Aromatic 200 | 3.0 | Toximul TANS-5 | 1.1 | nonionic blend | 0.9 |
| 1-36 | 36.0 | 17.9 | Exxate 1000 | 3.0 | Toximul TANS-5 | 1.1 | nonionic blend | 0.9 |
| 1-37 | 36.0 | 17.9 | Aromatic 200 Exxate 1000 | 1.5 1.5 | Toximul TANS-5 | 1.1 | nonionic blend | 0.9 |
| 1-38 | 36.0 | 17.9 | Aromatic 100 | 3.0 | Variquat 638 | 2.0 | none | |
| 1-39 | 36.0 | none | Aromatic 150 | 3.0 | Toximul TANS-5 | 1.1 | nonionic blend | 0.9 |
| 1-40 | 36.0 | none | Aromatic 100 | 3.0 | Toximul TANS-5 | 1.1 | nonionic blend | 0.9 |
| 1-41 | 44.0 | none | Aromatic 200 | 3.0 | none | | none | |
| 1-42 | 45.0 | none | | | Toximul TANS-5 | 1.1 | nonionic blend | 0.9 |
| 1-43 | 43.0 | none | Aromatic 200 | 3.0 | Toximul TANS-5 | 1.1 | nonionic blend | 0.9 |
| 1-44 | 36.0 | 17.9 | Exxate 1000 | 1.4 | Toximul TANS-5 | 1.1 | nonionic blend | 0.9 |
| 1-45 | 42.0 | 5.0 | Exxate 1000 | 1.5 | Toximul TANS-5 | 1.1 | nonionic blend | 0.9 |
| 1-46 | none | none | Exxate 1000 | 1.5 | Toximul TANS-5 | 1.1 | nonionic blend | 0.9 |

Example 2

Certain compositions described in Table 1 were analyzed for Silwet® L-77 content 28–32 days after their preparation. The concentration of Silwet® L-77 in the original composition and the concentration found in the aged samples by gravimetric analysis and by HPLC are shown in Table 2.

TABLE 2

| Composition | Initial L-77% (calculated) | Final L-77% gravimetric | Final L-77% HPLC |
|---|---|---|---|
| 1-26 | 14.4 | 14.5 | 14.2 |
| 1-27 | 14.4 | 14.3 | 14.2 |
| 1-28 | 0 | <0.1 | <0.1 |
| 1-29 | 14.4 | 14.1 | 13.9 |
| 1-30 | 14.4 | 13.4 | 12.9 |
| 1-31 | 14.4 | 14.3 | 13.9 |
| 1-34 | 19.6 | 20.1 | 20.7 |
| 1-37 | 17.9 | 17.7 | 17.5 |
| 1-38 | 17.9 | 17.9 | 17.4 |
| 1-39 | 17.9 | 17.6 | 17.7 |
| 1-40 | 17.9 | 19.7 | 17.6 |
| 1-41 | 0 | 0.2 | <0.1 |
| 1-42 | 0 | <0.1 | <0.1 |
| 1-43 | 0 | 0.1 | 0.1 |
| 1-44 | 17.9 | 17.7 | 17.6 |
| 1-45 | 5.0 | 4.8 | 4.9 |

Thus, compositions of the present invention exhibited good chemical stability, with little chemical degradation of the Silwet® L-77.

Example 3

Certain compositions described in Table 1 were analyzed for Silwet® L-77 content 29–33 days after their preparation. The concentration of Silwet® L-77 in the original composition and the concentration found in the aged samples by gravimetric analysis and by HPLC are shown in Table 3.

TABLE 3

| Composition | Initial L-77% (calculated) | Final L-77% gravimetric | Final L-77% HPLC |
|---|---|---|---|
| 1-26 | 14.4 | 14.5 | 14.0 |
| 1-27 | 14.4 | 14.4 | 14.1 |
| 1-31 | 14.4 | 13.9 | 13.8 |
| 1-32 | 14.4 | 14.6 | 14.7 |
| 1-33 | 14.4 | 14.7 | 14.0 |

Thus, as in Example 2, compositions of the present invention exhibited good chemical stability, with little chemical degradation of the Silwet® L-77.

Example 4

The following procedure was used for testing compositions to determine herbicidal effectiveness.

Seeds of the plant species indicated, in this example velvetleaf (*Abutilon theophrasti,* ABUTH) and Japanese millet, a variety of barnyardgrass (*Echinochloa crus-galli,* ECHCF), were planted in 85 mm square pots in a soil mix which was previously steam sterilized and prefertilized with a 14—14—14 NPK slow release fertilizer at a rate of 3.6 kg/m3. The pots were placed in a greenhouse with subirrigation. About one week after emergence, seedlings were thinned as needed, including removal of any unhealthy or abnormal plants, to create a uniform series of test pots.

The plants were maintained for the duration of the test in the greenhouse where they received a minimum of 14 hours of light per day. If natural light was insufficient to achieve the daily requirement, artificial light with an intensity of approximately 475 microeinsteins was used to make up the difference. Exposure temperatures were not precisely controlled but averaged about 27° C. during the day and about 18° C. during the night. Plants were sub-irrigated throughout the test to ensure adequate soil moisture levels.

Pots were assigned to different treatments in a filly randomized experimental design with three replications. A set of pots was left untreated as a reference against which effects of the treatments could later be evaluated.

Application of glyphosate compositions was made by spraying with a track sprayer fitted with a 9501E nozzle calibrated to deliver a spray volume of 93 liters per hectare (l/ha) at a pressure of 166 kilopascals (kPa). After treatment, pots were returned to the greenhouse until ready for evaluation.

Treatments were made using dilute aqueous compositions prepared by dilution with water of preformulated concentrate compositions of Table 1. Some treatments, for comparative purposes, involved adding Silwet® L-77 as a tank mix adjuvant to the dilute plant treatment composition.

For evaluation of herbicidal effectiveness, all plants in the test were examined by a single practiced technician, who recorded percent inhibition, a visual measurement of the effectiveness of each treatment by comparison with untreated plants. Inhibition of 0% indicates no effect, and inhibition of 100% indicates that all of the plants are completely dead. Inhibition of 85% or more is in most cases considered acceptable for normal herbicidal use; however in greenhouse tests such as those of the examples it is normal to apply compositions at rates which give less than 85% inhibition, as this makes it easier to discriminate among compositions having different levels of effectiveness.

In this example the compositions were applied to the plants 20 days after planting, and herbicidal inhibition was evaluated 15 days after treatment.

Results, averaged for all replicates of each treatment, are shown in Table 4.

TABLE 4

| Composition | glyphosate rate g.a.e./ha | tank mix additive name | % by volume | % inhibition ABUTH | % inhibition ECHCF |
|---|---|---|---|---|---|
| Formulation L | 200 | | | 48 | 27 |
| | 300 | | | 65 | 40 |
| | 400 | | | 73 | 45 |
| | 500 | | | 82 | 53 |
| Formulation J | 200 | | | 65 | 55 |
| | 300 | | | 73 | 65 |
| | 400 | | | 78 | 77 |
| | 500 | | | 83 | 87 |
| Formulation L | 200 | Silwet L-77 | 0.5 | 82 | 23 |
| | 300 | Silwet L-77 | 0.5 | 92 | 33 |
| | 400 | Silwet L-77 | 0.5 | 93 | 38 |
| | 500 | Silwet L-77 | 0.5 | 95 | 52 |
| Formulation J | 200 | Silwet L-77 | 0.5 | 80 | 28 |
| | 300 | Silwet L-77 | 0.5 | 83 | 42 |
| | 400 | Silwet L-77 | 0.5 | 90 | 42 |
| | 500 | Silwet L-77 | 0.5 | 94 | 48 |
| 1-1 | 200 | | | 67 | 40 |
| | 300 | | | 72 | 43 |
| | 400 | | | 77 | 48 |
| | 500 | | | 77 | 58 |
| 1-2 | 200 | | | 62 | 35 |
| | 300 | | | 67 | 38 |
| | 400 | | | 70 | 47 |
| | 500 | | | 72 | 57 |
| 1-3 | 200 | | | 70 | 30 |
| | 300 | | | 75 | 37 |
| | 400 | | | 80 | 53 |
| | 500 | | | 88 | 70 |
| 1-4 | 200 | | | 47 | 30 |
| | 300 | | | 65 | 40 |
| | 400 | | | 73 | 45 |
| | 500 | | | 80 | 52 |
| 1-5 | 200 | | | 48 | 42 |
| | 300 | | | 55 | 45 |
| | 400 | | | 60 | 52 |
| | 500 | | | 65 | 58 |
| 1-6 | 200 | | | 35 | 35 |
| | 300 | | | 43 | 53 |
| | 400 | | | 48 | 72 |
| | 500 | | | 58 | 77 |

Example 5

Velvetleaf (*Abutilon theophrasti,* ABUTH) and Japanese millet (*Echinochloa crus-galli,* ECHCF) plants were grown and treated by the standard procedures given above. Applications of spray compositions were made 18 days after planting, and evaluation of herbicidal inhibition was done 21 days after application. Results, averaged for all replicates of each treatment, are shown in Table 5.

TABLE 5

| Composition | glyphosate rate g.a.e./ha | tank mix additive name | % by volume | % inhibition ABUTH | % inhibition ECHCF |
|---|---|---|---|---|---|
| Formulation L | 200 | | | 43 | 63 |
| | 300 | | | 73 | 73 |
| | 400 | | | 82 | 85 |

TABLE 5-continued

| Composition | glyphosate rate g.a.e./ha | tank mix additive name | % by volume | % inhibition ABUTH | ECHCF |
|---|---|---|---|---|---|
| | 500 | | | 88 | 92 |
| Formulation J | 200 | | | 52 | 77 |
| | 300 | | | 80 | 97 |
| | 400 | | | 83 | 99 |
| | 500 | | | 95 | 99 |
| Formulation L | 200 | Silwet L-77 | 0.5 | 89 | 62 |
| | 300 | Silwet L-77 | 0.5 | 99 | 72 |
| | 400 | Silwet L-77 | 0.5 | 99 | 88 |
| | 500 | Silwet L-77 | 0.5 | 100 | 97 |
| Formulation J | 200 | Silwet L-77 | 0.5 | 97 | 68 |
| | 300 | Silwet L-77 | 0.5 | 99 | 73 |
| | 400 | Silwet L-77 | 0.5 | 99 | 97 |
| | 500 | Silwet L-77 | 0.5 | 100 | 98 |
| 1-12 | 200 | | | 87 | 98 |
| | 300 | | | 96 | 98 |
| | 400 | | | 99 | 99 |
| | 500 | | | 99 | 100 |
| 1-13 | 200 | | | 93 | 95 |
| | 300 | | | 96 | 98 |
| | 400 | | | 97 | 100 |
| | 500 | | | 100 | 100 |
| 1-14 | 200 | | | 77 | 87 |
| | 300 | | | 91 | 99 |
| | 400 | | | 97 | 99 |
| | 500 | | | 99 | 100 |
| 1-15 | 200 | | | 67 | 87 |
| | 300 | | | 88 | 94 |
| | 400 | | | 93 | 99 |
| | 500 | | | 96 | 100 |
| 1-16 | 200 | | | 67 | 82 |
| | 300 | | | 92 | 94 |
| | 400 | | | 97 | 99 |
| | 500 | | | 98 | 100 |
| 1-17 | 200 | | | 68 | 88 |
| | 300 | | | 82 | 88 |
| | 400 | | | 97 | 98 |
| | 500 | | | 97 | 98 |

Example 6

An aqueous composition containing the IPA salt of glyphosate (6.0% a.e.) was prepared containing 3.0% Silwet® L-77. This composition was used as a standard against which to compare the ability of certain compositions described above to permeate through a PTFE filter membrane.

Four compositions of the invention were diluted to 6% glyphosate a.e. for comparison with the standard. For each composition, 2 μl was applied to the top (shiny) surface of a PTFE filter resting horizontally on top of a black plastic bottle cap. The time that passed between first contact of the solution with the filter and permeation therethrough was recorded. The results (average ± standard deviation of three replicates, or twelve replicates in the case of the standard) are summarized in Table 6.

TABLE 6

| Composition | Permeation time of composition (sec) | Permeation time of standard (sec) | Delay (sec) |
|---|---|---|---|
| 1-3 | 134.3 ± 12.1 | 10.2 ± 2.3 | 124.1 |
| 1-12 | 174.9 ± 16.1 | | 164.7 |
| 1-34 | 19.2 ± 4.4 | | 9.2 |
| 1-35 | 80.3 ± 4.7 | | 70.1 |

Thus, compositions of the present invention exhibited significantly delayed permeation as compared to a simple tank mix formulation of glyphosate and Silwet® L-77. Note that Composition 1-34, which showed the shortest delay, contained Silwet® L-77 at a higher concentration relative to glyphosate than the other three compositions or the standard.

Example 7

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting, and bition was done 22 days after application. Results, averaged for all replicates of each treatment, are shown in Table 7.

TABLE 7

| Composition | glyphosate rate g.a.e./ha | tank mix additive name | % by volume | % inhibition ABUTH | ECHCF |
|---|---|---|---|---|---|
| Formulation L | 200 | | | 27 | 55 |
| | 400 | | | 67 | 78 |
| | 600 | | | 83 | 97 |
| | 800 | | | 98 | 99 |
| Formulation J | 200 | | | 40 | 87 |
| | 400 | | | 77 | 99 |
| | 600 | | | 96 | 100 |
| | 800 | | | 98 | 100 |
| Formulation L | 200 | Silwet L-77 | 0.5 | 45 | 45 |
| | 400 | Silwet L-77 | 0.5 | 94 | 77 |
| | 600 | Silwet L-77 | 0.5 | 96 | 92 |
| | 800 | Silwet L-77 | 0.5 | 100 | 98 |
| Formulation J | 200 | Silwet L-77 | 0.5 | 55 | 73 |
| | 400 | Silwet L-77 | 0.5 | 82 | 86 |
| | 600 | Silwet L-77 | 0.5 | 96 | 99 |
| | 800 | Silwet L-77 | 0.5 | 99 | 100 |
| 1-26 | 200 | | | 45 | 60 |
| | 400 | | | 75 | 80 |
| | 600 | | | 92 | 99 |
| | 800 | | | 100 | 100 |
| 1-27 | 200 | | | 40 | 55 |
| | 400 | | | 67 | 83 |
| | 600 | | | 90 | 100 |
| | 800 | | | 94 | 99 |
| 1-28 | 200 | | | 30 | 78 |
| | 400 | | | 67 | 95 |
| | 600 | | | 82 | 99 |
| | 800 | | | 97 | 100 |
| 1-29 | 200 | | | 43 | 77 |
| | 400 | | | 75 | 97 |
| | 600 | | | 95 | 100 |
| | 800 | | | 100 | 100 |
| 1-30 | 200 | | | 48 | 80 |
| | 400 | | | 73 | 89 |
| | 600 | | | 93 | 100 |
| | 800 | | | 100 | 100 |
| 1-31 | 200 | | | 52 | 83 |
| | 400 | | | 93 | 97 |
| | 600 | | | 99 | 100 |
| | 800 | | | 100 | 100 |
| 1-32 | 200 | | | 47 | 87 |
| | 400 | | | 84 | 97 |
| | 600 | | | 98 | 100 |
| | 800 | | | 100 | 100 |
| 1-33 | 200 | | | 43 | 80 |
| | 400 | | | 85 | 97 |
| | 600 | | | 99 | 100 |
| | 800 | | | 100 | 100 |
| 1-34 | 200 | | | 70 | 87 |
| | 400 | | | 96 | 96 |
| | 600 | | | 100 | 100 |
| | 800 | | | 100 | 99 |
| 1-35 | 200 | | | 63 | 82 |
| | 400 | | | 98 | 87 |
| | 600 | | | 100 | 100 |
| | 800 | | | 100 | 99 |
| 1-36 | 200 | | | 60 | 82 |
| | 400 | | | 78 | 94 |

TABLE 7-continued

| Composition | glyphosate rate g.a.e./ha | tank mix additive name | % by volume | % inhibition ABUTH | ECHCF |
|---|---|---|---|---|---|
|  | 600 |  |  | 98 | 100 |
|  | 800 |  |  | 100 | 99 |
| 1-37 | 200 |  |  | 53 | 78 |
|  | 400 |  |  | 83 | 94 |
|  | 600 |  |  | 97 | 100 |
|  | 800 |  |  | 100 | 99 |
| 1-38 | 200 |  |  | 55 | 78 |
|  | 400 |  |  | 92 | 97 |
|  | 600 |  |  | 100 | 100 |
|  | 800 |  |  | 100 | 99 |
| 1-39 | 200 |  |  | 53 | 73 |
|  | 400 |  |  | 80 | 93 |
|  | 600 |  |  | 96 | 100 |
|  | 800 |  |  | 100 | 100 |
| 1-40 | 200 |  |  | 50 | 75 |
|  | 400 |  |  | 92 | 93 |
|  | 600 |  |  | 100 | 99 |
|  | 800 |  |  | 100 | 99 |
| 1-41 | 200 |  |  | 27 | 70 |
|  | 400 |  |  | 67 | 88 |
|  | 600 |  |  | 80 | 98 |
|  | 800 |  |  | 82 | 99 |
| 1-42 | 200 |  |  | 28 | 75 |
|  | 400 |  |  | 70 | 93 |
|  | 600 |  |  | 82 | 100 |
|  | 800 |  |  | 87 | 100 |
| 1-43 | 200 |  |  | 30 | 80 |
|  | 400 |  |  | 72 | 98 |
|  | 600 |  |  | 70 | 100 |
|  | 800 |  |  | 83 | 100 |

Example 8

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting, and evaluation of herbicidal inhibition was done 12 days after application. Results, averaged for all replicates of each treatment, are shown in Table 8.

TABLE 8

| Composition | glyphosate rate g.a.e./ha | tank mix additive name | % by volume | % inhibition ABUTH | ECHCF |
|---|---|---|---|---|---|
| Formulation L | 200 |  |  | 57 | 48 |
|  | 400 |  |  | 83 | 53 |
|  | 600 |  |  | 93 | 63 |
|  | 800 |  |  | 96 | 80 |
| Formulation J | 200 |  |  | 77 | 65 |
|  | 400 |  |  | 90 | 80 |
|  | 600 |  |  | 97 | 85 |
|  | 800 |  |  | 99 | 92 |
| Formulation L | 200 | Silwet L-77 | 0.5 | 80 | 40 |
|  | 400 | Silwet L-77 | 0.5 | 85 | 52 |
|  | 600 | Silwet L-77 | 0.5 | 90 | 60 |
|  | 800 | Silwet L-77 | 0.5 | 98 | 70 |
| Formulation J | 200 | Silwet L-77 | 0.5 | 98 | 50 |
|  | 400 | Silwet L-77 | 0.5 | 98 | 70 |
|  | 600 | Silwet L-77 | 0.5 | 99 | 78 |
|  | 800 | Silwet L-77 | 0.5 | 99 | 83 |
| 1-26 | 200 |  |  | 92 | 50 |
|  | 400 |  |  | 96 | 57 |
|  | 600 |  |  | 98 | 63 |
|  | 800 |  |  | 98 | 63 |
| 1-27 | 200 |  |  | 94 | 50 |
|  | 400 |  |  | 98 | 68 |
|  | 600 |  |  | 98 | 92 |
|  | 800 |  |  | 99 | 78 |
| 1-28 | 200 |  |  | 63 | 60 |
|  | 400 |  |  | 83 | 65 |
|  | 600 |  |  | 86 | 87 |
|  | 800 |  |  | 95 | 94 |
| 1-29 | 200 |  |  | 95 | 55 |
|  | 400 |  |  | 99 | 87 |
|  | 600 |  |  | 99 | 91 |
|  | 800 |  |  | 99 | 93 |
| 1-30 | 200 |  |  | 97 | 80 |
|  | 400 |  |  | 98 | 82 |
|  | 600 |  |  | 99 | 87 |
|  | 800 |  |  | 99 | 90 |
| 1-31 | 200 |  |  | 87 | 67 |
|  | 400 |  |  | 98 | 83 |
|  | 600 |  |  | 99 | 93 |
|  | 800 |  |  | 99 | 96 |
| 1-34 | 200 |  |  | 95 | 82 |
|  | 400 |  |  | 99 | 88 |
|  | 600 |  |  | 99 | 94 |
|  | 800 |  |  | 99 | 99 |
| 1-35 | 200 |  |  | 93 | 82 |
|  | 400 |  |  | 97 | 90 |
|  | 600 |  |  | 99 | 93 |
|  | 800 |  |  | 100 | 91 |
| 1-36 | 200 |  |  | 88 | 75 |
|  | 400 |  |  | 97 | 87 |
|  | 600 |  |  | 99 | 93 |
|  | 800 |  |  | 99 | 96 |
| 1-37 | 200 |  |  | 88 | 70 |
|  | 400 |  |  | 97 | 92 |
|  | 600 |  |  | 98 | 96 |
|  | 800 |  |  | 98 | 97 |
| 1-38 | 200 |  |  | 98 | 87 |
|  | 400 |  |  | 98 | 95 |
|  | 600 |  |  | 99 | 96 |
|  | 800 |  |  | 97 | 92 |
| 1-39 | 200 |  |  | 87 | 70 |
|  | 400 |  |  | 95 | 82 |
|  | 600 |  |  | 97 | 90 |
|  | 800 |  |  | 98 | 96 |
| 1-40 | 200 |  |  | 87 | 67 |
|  | 400 |  |  | 95 | 87 |
|  | 600 |  |  | 96 | 88 |
|  | 800 |  |  | 98 | 95 |
| 1-41 | 200 |  |  | 70 | 63 |
|  | 400 |  |  | 78 | 62 |
|  | 600 |  |  | 90 | 68 |
|  | 800 |  |  | 93 | 85 |
| 1-42 | 200 |  |  | 70 | 65 |
|  | 400 |  |  | 87 | 70 |
|  | 600 |  |  | 92 | 83 |
|  | 800 |  |  | 97 | 92 |
| 1-43 | 200 |  |  | 75 | 65 |
|  | 400 |  |  | 90 | 65 |
|  | 600 |  |  | 90 | 87 |
|  | 800 |  |  | 92 | 90 |
| 1-44 | 200 |  |  | 88 | 75 |
|  | 400 |  |  | 99 | 92 |
|  | 600 |  |  | 100 | 98 |
|  | 800 |  |  | 100 | 95 |
| 1-45 | 200 |  |  | 83 | 87 |
|  | 400 |  |  | 91 | 93 |
|  | 600 |  |  | 98 | 97 |
|  | 800 |  |  | 98 | 99 |

Example 9

Compositions 9-1, 9-2, 9-3, and 9-4 of the present invention were prepared with the following ingredients:

Composition 9-1:

IPA glyphosate, 35.6% a.e.
Silwet ® L-77, 17.9%
Toximul ™ TANS-5, 1.1%
nonionic blend as in Table 1, 0.9%
Aromatic 200, 3.0%

Composition 9-2:

IPA glyphosate, 33.9% a.e.
Silwet ® L-77, 19.5%
Variquat ™ 638, 2.0%
Toximul ™ TANS-5, 1.1%
nonionic blend as in Table 1, 0.9%
Aromatic 200, 3.0%

Composition 9-3:

IPA glyphosate, 34.2% a.e.
Silwet ® L-77, 19.6%
Variquat ™ 638, 1.0%
Toximul ™ TANS-5, 1.1%
nonionic blend as in Table 1, 0.9%
Aromatic 200, 3.0%

Composition 9-4:

IPA glyphosate, 33.9% a.e.
Silwet ® L-77, 19.5%
Variquat ™ 638, 2.0%
Toximul ™ TANS-5, 1.1%
nonionic blend as in Table 1, 0.9%
Aromatic 100, 3.0%

The balance of compositions 9-1, 9-2, 9-3 and 9-4 was water.

Comparative formulations C-1 and C-2 were prepared with the following ingredients.

Composition C-1:

IPA glyphosate, 15.0% a.e.
Silwet ® L-77, 2.5%
Aromox ™ DMMC-W, 10.0%

Composition C-2:

IPA glyphosate, 15.0% a.e.
Silwet ® L-77, 17.0%
Aromox ™ DMMC-W, 10.0%
Aromox ™ DMMC-W is a dimethylcocoamine oxide of Akzo.

The balance of compositions C-1 and C-2 was water. Composition C-1 is substantially the same as the composition described in Example 3 of Australian Patent No. 658150. Composition C-2 is a modified version of that same composition with a Silwet® L-77 concentration more nearly similar to those of the above-described compositions of the present invention.

Compositions 9-1, 9-2, 9-3, and 9-4 were placed in an oven at 50° C. and sampled for analysis after 11 days. Compositions C-1 and C-2 were separately placed in an oven at 50° C. and sampled for analysis after 9 days. The results of the analysis are shown in Table 9.

TABLE 9

| Formulation | % L-77 expected | % L-77 found | % loss of L-77 |
|---|---|---|---|
| 9-1 | 17.9 | 18.3 | 0 |
| 9-2 | 19.5 | 19.3 | 1 |
| 9-3 | 19.6 | 21.4 | 0 |
| 9-4 | 19.5 | 20.1 | 0 |

TABLE 9-continued

| Formulation | % L-77 expected | % L-77 found | % loss of L-77 |
|---|---|---|---|
| C-1 | 2.50 | 1.95 | 22 |
| C-2 | 17.0 | 13.8 | 19 |

Thus, chemical degradation of Silwet® L-77 was very significant in compositions C-1 and C-2 over a nine-day period at 50° C., whereas in the compositions of the present invention Silwet® L-77 was essentially stable over a slightly longer period of time under the same conditions.

The preceding description of specific embodiments of the present invention is not intended to be a complete list of every possible embodiment of the invention. Persons skilled in this field will recognize that modifications can be made to the specific embodiments described here that would be within the scope of the present invention.

What is claimed is:

1. A liquid composition for application of a water-soluble exogenous chemical substance to foliage of a plant following dilution in a suitable volume of water, comprising a continuous aqueous phase, wherein is dissolved said water-soluble exogenous chemical substance in an amount which is biologically effective when the composition is diluted in said suitable volume of water and applied to said foliage, and wherein is dispersed a discontinuous oil phase that comprises (a) an adjuvant amount of a siloxane surfactant of formula (I)

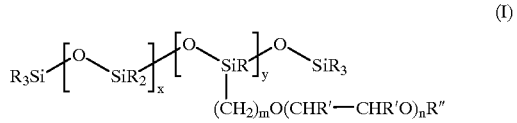

where x is an integer or average of integers of 0 to about 100, y is an integer or average of integers of 1 to about 30, each m is independently an integer of 1 to about 20, each n is independently an integer of 1 to about 30, each R group is independently a hydrogen or $C_{1-6}$ hydrocarbyl group, each R' group is independently a hydrogen or $C_{1-4}$ alkyl group, and each R" group is independently a hydrogen $C_{1-20}$ hydrocarbyl or an acyl group, and (b) a substantially water-insoluble organic solvent for said siloxane surfactant, said organic solvent being selected from alkyl naphthalenic aromatic solvents and alkyl acetates and present in an amount such that substantially all of said siloxane surfactant is contained in or associated with said oil phase.

2. A composition of claim 1 that is an oil-in-water emulsion wherein said discontinuous oil phase is stably dispersed in said continuous aqueous phase, and that further comprises a stabilizing amount of an emulsifying system having one or more emulsifiers.

3. A composition of claim 1 wherein said siloxane surfactant is a micropore infiltrant and is present in the composition in an amount which, upon dilution in said suitable volume of water, provides an infiltrating effective concentration of said siloxane surfactant.

4. A composition of claim 1 wherein, in the formula for said siloxane surfactant, x is an integer or average of integers of 0 to about 10, y is an integer or average of integers of 1 to about 10, m is an integer of 2 to 6, n is about 5 to about 20, all R' groups are hydrogen, and R and R" groups are independently selected from hydrogen and $C_{1-4}$ alkyl groups.

5. A composition of claim 4 wherein, in the formula for said siloxane surfactant, x is 0 or 1, y is 1, and R and R"

groups are independently selected from hydrogen and methyl groups.

6. A composition of claim 5 wherein, in the formula for said siloxane surfactant, x is 0, m is 3, and R groups are methyl groups.

7. A composition of claim 1 wherein said water-soluble exogenous chemical substance is N-phosphonomethylglycine in the form of one or more salts thereof and is present in an amount which is herbicidally effective when the composition is diluted in said suitable volume of water and applied to said foliage.

8. A composition of claim 7 wherein said N-phosphonomethylglycine is present in a concentration of about 50 to about 500 g a.e./l in the composition as a whole.

9. A composition of claim 7 wherein said N-phosphonomethylglycine is present in a concentration of about 300 to about 500 g a.e./l in the composition as a whole.

10. A composition of claim 7 wherein said siloxane surfactant and said N-phosphonomethylglycine are present in a weight ratio of about 1:20 to about 5:1.

11. A composition of claim 7 wherein said siloxane surfactant and said N-phosphonomethylglycine are present in a weight ratio of about 1:10 to about 1:1.

12. A composition of any of claims 7 to 11 wherein, in the formula for said siloxane surfactant, x is 0, y is 1, m is 3, n is about 5 to about 20, R groups are methyl groups, R' groups are hydrogen and R" is a hydrogen or methyl group.

13. A composition of claim 1 wherein the organic solvent is selected such that said organic solvent and said siloxane surfactant are sufficiently cosoluble to form a solution having a weight/weight ratio of organic solvent to siloxane surfactant in at least part of the range from 10:1 to 1:10.

14. A composition of claim 1 wherein the organic solvent is selected such that said organic solvent and said siloxane surfactant are sufficiently cosoluble to form a solution having a weight/weight ratio of organic solvent to siloxane surfactant of 1:5 to 1:10.

15. A composition of any of claims 7–12 wherein the organic solvent is an aromatic solvent.

16. A method for eliciting a biological effect in a plant comprising diluting a composition of claim 1 in a suitable volume of water to form a plant treatment composition, and applying the plant treatment composition to foliage of the plant.

17. A method for killing or controlling plants comprising diluting a composition of any of claims 7–12 in a suitable volume of water to form a plant treatment composition, and applying the plant treatment composition to foliage of the plants.

18. A method for killing or controlling plants comprising diluting a composition of any of claims 7–12 in water to form a plant treatment composition, and applying the plant treatment composition to foliage of the plants at a rate of about 25 to about 1000 liters per hectare containing about 100 to about 2500 grams per hectare of N-phosphonomethylglycine acid equivalent.

* * * * *